(12) United States Patent
Sweet

(10) Patent No.: US 10,451,455 B2
(45) Date of Patent: Oct. 22, 2019

(54) WIRELESS SENSOR FOR DETECTION AND MEASUREMENT OF PROPERTIES IN LIQUIDS OVER AN INTERNET-BASED NETWORK

(71) Applicant: SAPERE SYSTEMS INCORPORATED, St. Helena, CA (US)

(72) Inventor: Phillips Sweet, Laguna Beach, CA (US)

(73) Assignee: SAPERE SYSTEMS INCORPORATED, St. Helena, CA (US)

(*) Notice: Subject to any disclaimer, the term of this patent is extended or adjusted under 35 U.S.C. 154(b) by 0 days.

(21) Appl. No.: 15/814,369

(22) Filed: Nov. 15, 2017

(65) Prior Publication Data

US 2018/0136020 A1 May 17, 2018

Related U.S. Application Data

(60) Provisional application No. 62/422,446, filed on Nov. 15, 2016.

(51) Int. Cl.
*G01D 21/02* (2006.01)
*H04W 84/18* (2009.01)
(Continued)

(52) U.S. Cl.
CPC ........... *G01D 21/02* (2013.01); *G01N 33/146* (2013.01); *H04L 67/10* (2013.01); *H04L 67/12* (2013.01); *H04W 84/18* (2013.01); *G01N 27/414* (2013.01)

(58) Field of Classification Search
CPC .................................................. G01N 33/146
See application file for complete search history.

(56) References Cited

U.S. PATENT DOCUMENTS

2004/0076946 A1* 4/2004 Trauner ............... G01N 33/146
435/3
2004/0126279 A1* 7/2004 Renzi ................ B01L 3/502715
422/502

(Continued)

OTHER PUBLICATIONS

Jordan Bartroli et al, Determination of Total and Free Sulfer Dioxide in Wine by Flow Injection Analysis and Gas Diffusion using p-Aminozobenzene as the Colorimetric Reagent.
(Continued)

*Primary Examiner* — Laura N Nguyen
(74) *Attorney, Agent, or Firm* — Rutan & Tucker, LLP; Kyle M. St. James

(57) ABSTRACT

The present invention is related to a wireless sensor that combines semiconductor technology with chemical diffusion in order to measure specific chemical and physical properties such as pH, acid level, SO2, temperature and liquid level of a target liquid in a container, and wirelessly delivers all the data to an internet-based computing network where the data can be accessed by an end user using a device connected to the internet, and a method to measure and analyze the chemical and physical properties of a target liquid using the wireless sensor, the method comprising immerging the wireless sensor into the target liquid in the container, measuring the chemical and physical properties of the target liquid, obtaining and analyzing data wirelessly through an internet-based computing network, wherein the target liquid can be an aqueous solution such as wine, spirits and beer.

20 Claims, 5 Drawing Sheets

(51) Int. Cl.
*H04L 29/08* (2006.01)
*G01N 33/14* (2006.01)
*G01N 27/414* (2006.01)

(56) References Cited

U.S. PATENT DOCUMENTS

| | | | |
|---|---|---|---|
| 2006/0032548 A1* | 2/2006 | Cupples | G01F 23/164 141/95 |
| 2011/0236963 A1* | 9/2011 | Burke | G01N 27/3274 435/287.1 |
| 2014/0081580 A1* | 3/2014 | Kim | G01N 33/146 702/24 |
| 2015/0198474 A1* | 7/2015 | Howard | C12G 1/00 702/55 |
| 2015/0253174 A1* | 9/2015 | Barrett | G01F 23/263 73/304 C |
| 2016/0367991 A1* | 12/2016 | Petersen | B01L 3/502 |
| 2017/0356871 A1* | 12/2017 | Hennings | G01N 27/416 |

OTHER PUBLICATIONS

GVWP04700 | Durapore Membrane Filter, Merck KGaA, Darmstadt, Germany.
S. Alegret, et al, Flow-Through pH-ISFET as Detector in Automated Determinations, 1991, p. 349-354.
Jimenez-Jorquera, et al, ISFET Based Microsensors for Environmental Monitoring, Sensors, 2010, Barcelona, Spain.
Mainwaring, Wireless Sensor Networks for Habitat Monitoring, 2002, p. 88-97, Berkeley, USA.

\* cited by examiner

WIRELESS SENSOR FOR DETECTION AND MEASUREMENT OF PROPERTIES IN LIQUIDS OVER AN INTERNET-BASED NETWORK

The current application claims a priority to the U.S. Provisional Patent Application Ser. No. 62/422,446, filed on Nov. 15, 2016.

FIELD OF THE INVENTION

This invention relates to the field of detecting and measuring chemical and physical properties of a target liquid using a wireless sensor over cloud computing based network. Specifically, the measurement of specific chemical and physical properties (e.g., pH, or temperature) of a target liquid including alcoholic beverages such as wine, beer and spirits during fermentation and storage.

BACKGROUND OF THE INVENTION

Wireless sensors are used in many industries to provide convenient and useful ways of obtaining data. Examples include remote sensors to monitor water quality, health care devices that monitor a patient's condition and send data to their doctor without the need to be at the doctor's office, home security and energy use sensors to give consumers and businesses real time data without the need to be physically at the location where the sensing is taking place, and applying wireless sensor networks to real world habitat monitoring (1).

Internet-based computing networks used in combination with wireless sensors allow users to access real time data on wireless devices such as cell phones and tablet devices.

Silicon based computer chips can be used to detect properties of liquids that come in contact with the chip surface by measuring the electrical current change produced as a result of the interaction. One chip called an ISFET (ion selective field effect transistor), measures the free hydrogen ions in a liquid sample allowing for the measurement of the liquid's pH value (2, 3). It has been reported that ISFET-based microsensors that are based on semiconductor technology are used for monitoring of environmental parameters, and the technology used allows integration of circuitry and multiple sensors in the same substrate and accordingly they can be implemented in compact probes for particular applications, e.g., in situ monitoring and/or on-line measurements (2). Ion Selective Field Effect Transistors (ISFETs) are particularly helpful for measuring pH and other ions in small volumes and they can be integrated in compact flow cells for continuous measurements (2). Another report has shown that the implementation of a pH-ISFET planar chip in a flow-injection system by means of a specially designed flow cell and the application of the sensor to the analysis of volatile compounds is described, where ammonia and sulfur dioxide are determined by exploiting the advantages of the flow techniques combined with continuous gas filtration, initial species are converted to gaseous compounds, which diffuse through a microporous hydrophobic membrane into an ammonium chloride or hydrogen sulfite recipient stream, producing a pH variation that is monitored by the semiconductor detector (3).

Membranes can be used to separate molecules in a liquid into a liquid or gas form by only allowing certain molecules to pass through the membrane. The resulting molecules can then be measured separate from the original liquid. Combining certain chemistries together allows for controlled diffusion across the membrane. In winemaking and the making of alcoholic beverages such as spirits, beer and cider, it is important to continually measure and monitor physical and chemical properties of the beverage during fermentation and aging as the properties are susceptible to change, especially when stored in wooden barrels. This process involves taking samples for analysis by a lab using specialized lab equipment.

Prior art lacks any way to obtain information about the wine or spirits in a barrel or container without manually drawing a sample from the container and running the sample through various tests in a laboratory using specialized equipment. This is problematic because the chemical make-up of alcoholic beverages can be continually changing even during storage. Accordingly, a need exists to test the wine or spirits at the barrel or container using a sensor that is able to wirelessly transmit the test data to an internet-based computer server where the data can then be accessed without any human interaction with the wine or spirits.

SUMMARY OF THE INVENTION

The present invention is related to a wireless sensor that combines semiconductor technology with chemical diffusion in order to measure specific chemical changes in a target liquid, such as wine, wherein the wireless sensor comprises an ion selective field effect transistor (ISFET). The sensor also contains technology that measures the physical properties such as pH, temperature and liquid level of the target liquid in a container, and wirelessly delivers all the data to an internet-based computing network where the data can be accessed by an end user using a device connected to the internet. While wine is used as an example of the target liquid, the target liquid is not limited to an alcoholic beverage such as wine, spirits and beer. Other examples include but are not limited to juices, milk, fuel, water, and biomedical fluids where wireless testing for specific chemistry and physical properties of the target liquid without any human interaction is desired.

Thus, one objective of the present invention is directed to a wireless sensor that combines semiconductor technology with chemical diffusion in order to measure specific chemical and physical properties in a target liquid, wherein the wireless sensor comprises an ion selective field effect transistor (ISFET). Another object is directed to a method to measure and analyze the chemical and physical properties of a target liquid such as wine, spirits and beer, the method comprising of immerging the wireless sensor or a probe connected to the wireless sensor into the target liquid in the container, measuring the chemical and physical properties, and obtaining and analyzing data wirelessly through an internet-based computing network. While wine, spirits or beer is used as an example for the target liquid, the target liquid is not limited to an alcoholic beverage such as wine, spirits and beer. The method can further comprise a step of alerting the user when certain changes in the liquid's chemistry or physical properties have occurred.

DETAIL DESCRIPTION OF THE INVENTION

Figure 1:
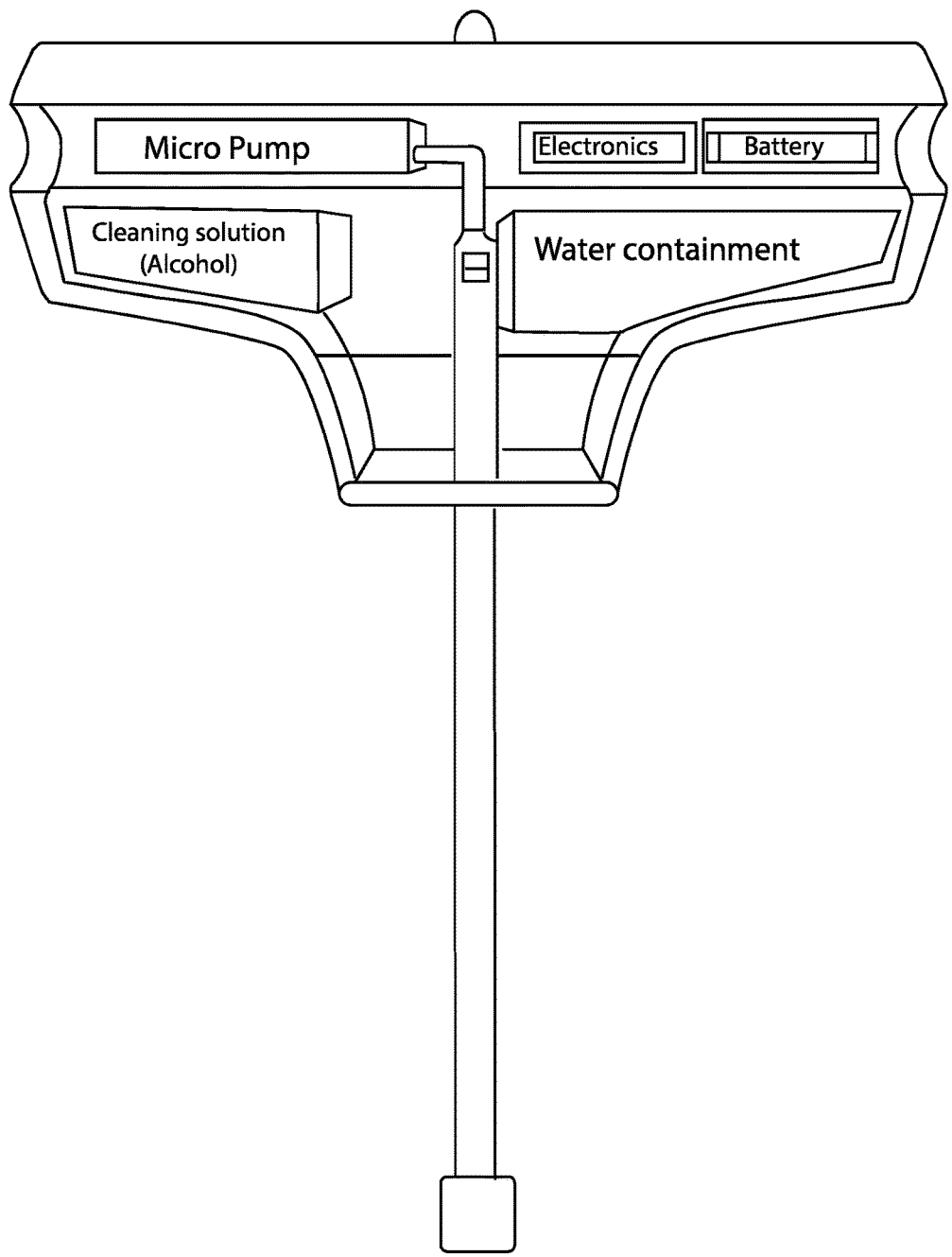
FIG. 1 represents a drawing of the basic components of the invention (i.e., the wireless sensor) without showing the chamber diagram which is shown in FIG. 3. Some basic components such as micro pump, electronics, battery, a waste containment area, and a replaceable cartridge containing cleaning solution are shown in the sensor.
Figure 2:
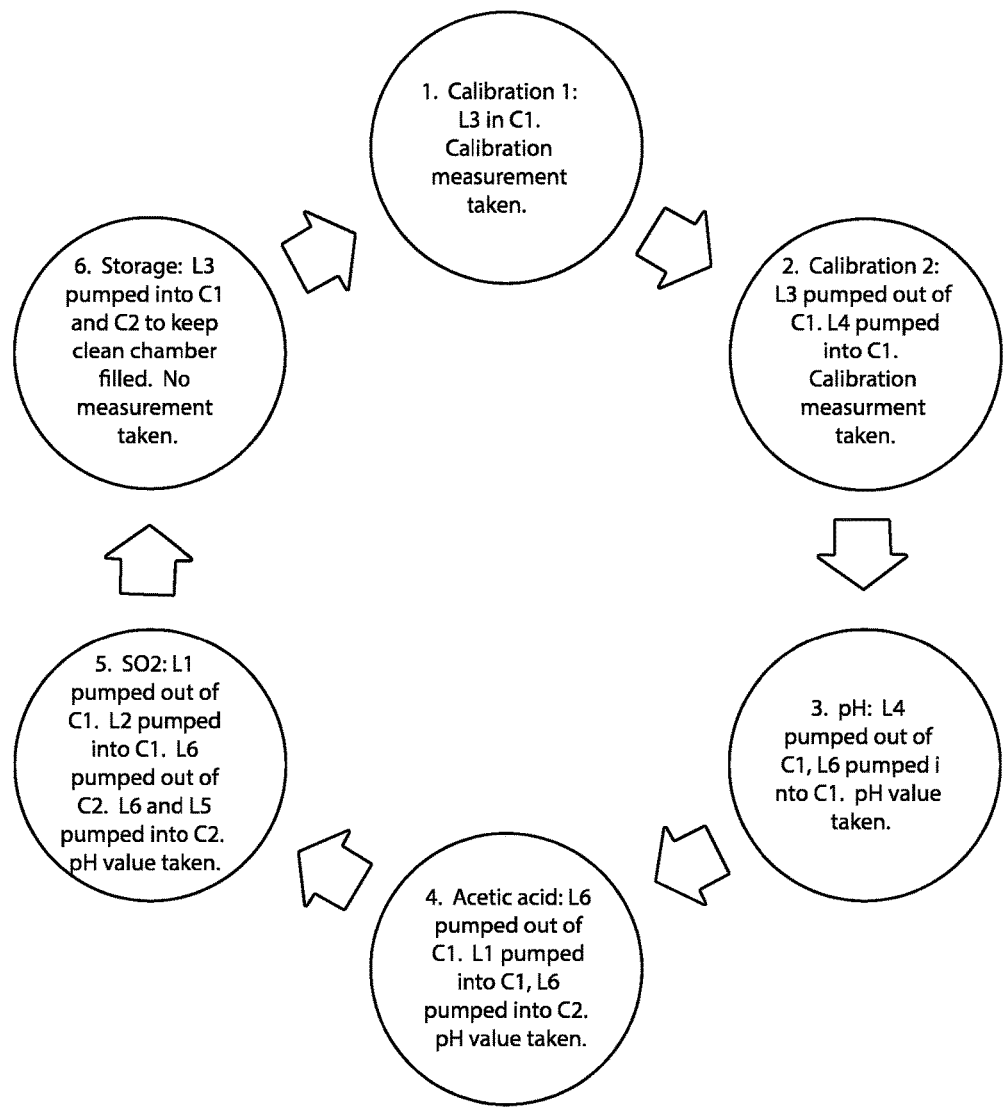
FIG. 2 is a flow diagram showing the flow of liquids that are required in order for the sensor to detect specific chemistries in the target liquid such as wine. Liquids enter into chambers 1 and chamber 2 of the invention (i.e., the wireless sensor) in a particular sequence in order to take a desired measurement of a target chemical such as acetic acid and SO$_2$ using the ISFET located in chamber 1.

The sensor is comprised of an enclosure in a form factor suited to the container which holds the target liquid. In the case of a target liquid stored in a barrel, the sensor enclosure is mounted on top of a bung or similar apparatus that is integrated into the enclosure and used to seal off the container in which a target liquid resides (FIG. 1). The target liquid can be any aqueous solution and is not limited to an alcoholic beverage such as wine, spirits and beer. In the case of a typical wine barrel, the sensor containing the integrated bung sits on top of the barrel with the bung portion resting inside a hole at the top and center of the barrel. Inside of the enclosure contains a ISFET semiconductor chip, two or more chambers separated by permeable membranes, a valve system, a pump system, a replaceable cartridge containing various fluids and an open waste containment area, a liquid level sensor, an accelerometer or similar movement detection technology, a printed circuit board with software used to run the components, a semiconductor chip capable of two-way communication, and a battery (FIG. 1). One or more probes are connected to the electronics or pump system, as applicable, and run through the center of the bung and protrude out several inches from the bottom of the bung and are submerged in the target liquid when the sensor is installed. The target liquid, such as wine in a barrel, is drawn up from the container through a probe and into one of the chambers through the valve system in a particular sequence. Liquids from the cartridge are drawn into one or more of the chambers in a particular sequence as well, and the ISFET chip, located in one of the chambers, takes measurements at specific times (see FIG. 2). In the case of a target liquid stored in bulk in a vessel such as a large tank, container or bladder, the sensor is designed to be sealed and placed directly into the target liquid to allow for measurements to be taken while immersed in the target liquid. Data collected by the sensor is transmitted using a wireless data transmitter on a communications protocol such as Bluetooth or Zigbee to an internet-based computing network where the data can be accessed by an end user using a device connected to the internet.

One example is to measure the acetic acid level in wine during the winemaking process using a wireless sensor.

Acetic acid is a weak monoprotic acid. In aqueous solution, it has a pKa value of 4.76. Its conjugate base is acetate (CH$_3$COO$^-$) and the acid-base equilibrium is defined by:

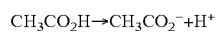

Figure 3:
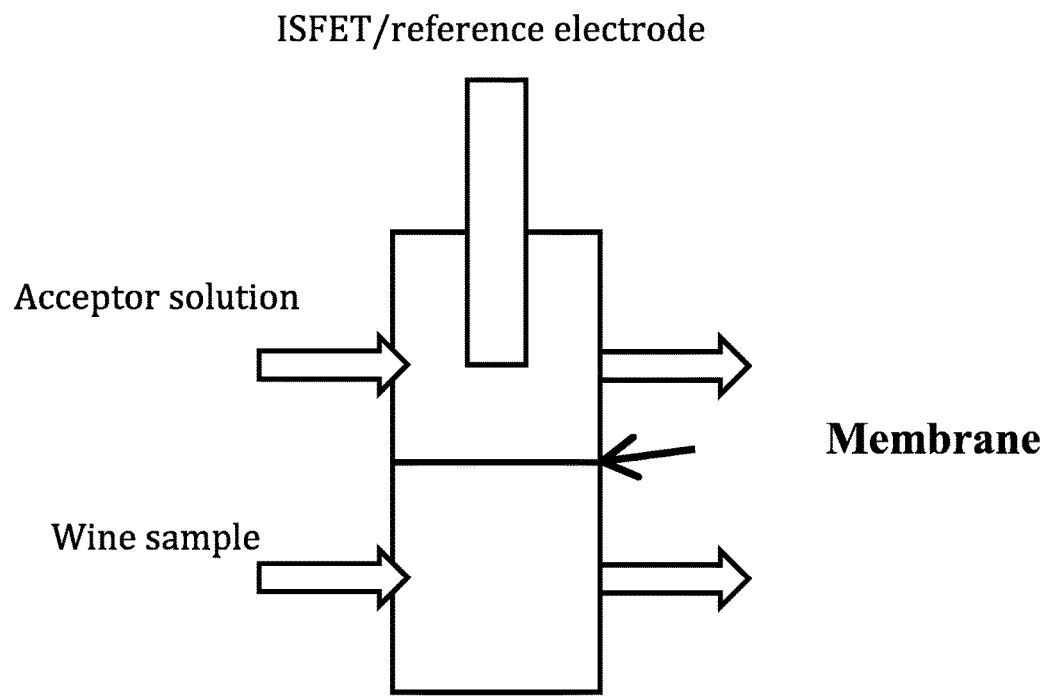
FIG. 3 represents a diagram of the diffusion process between chamber 1 and chamber 2 using wine in order to measure the level of acetic acid in the wine. An acetic acid acceptor solution in chamber 1 and wine in chamber 2 allows for the acetic acid molecules in the wine from chamber 2 to pass through the membrane into the acetic acid acceptor solution in chamber 1 where the pH is measured.

The pH in wine is within the range of 3-3.5. Therefore, acetic acid is basically in its acidic form. These two characteristics could be exploited to separate this acid from the other components of wine using a diffusion membrane permeable to acetic acid species. The wireless sensor contains two chambers (or compartments) separated by a diffusion membrane (see FIG. 3) and the wine sample is in the compartment 2, and in the compartment 1 there is an acetate solution (acceptor solution), there will be a diffusion of the acetic acid from the wine sample to the other side of the membrane. This acetic acid diffused through the membrane will produce a change of pH that could be detected by the pH ISFET. This pH change is dependent of the analyte concentration.

Another example is to measure the level of SO$_2$ during winemaking process using a wireless sensor.

Sulfur dioxide (SO$_2$) is typically used as an antioxidant and antiseptic in winemaking. This substance occurs in two different forms in wine: 1) free SO$_2$, formed by dissolving gas SO$_2$ in aqueous solution and bisulfite ion, HSO$_3^-$, the actual active fraction, and 2) complexed to aldehyde and ketone groups (basically acetaldehyde, with which it forms hydroxysulfonates). The sum of both forms is referred as total SO$_2$ (4). It has been reported that determination of total and free sulfur dioxide in wine by flow injection analysis and gas-diffusion using p-aminoazobenzene as the colorimetric reagent (4).

There is an acid-base equilibrium of sulfur dioxide, bisulfite and sulfite according to:

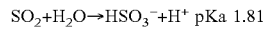

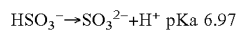

In wine, the free form is constituted by the equilibrium between molecular SO$_2$ and bisulfite, but the majority form is bisulfite ion. For example, when a wine has a pH of 2.8, only the 10% of the bisulfite is in the sulfur dioxide form.

Figure 4:
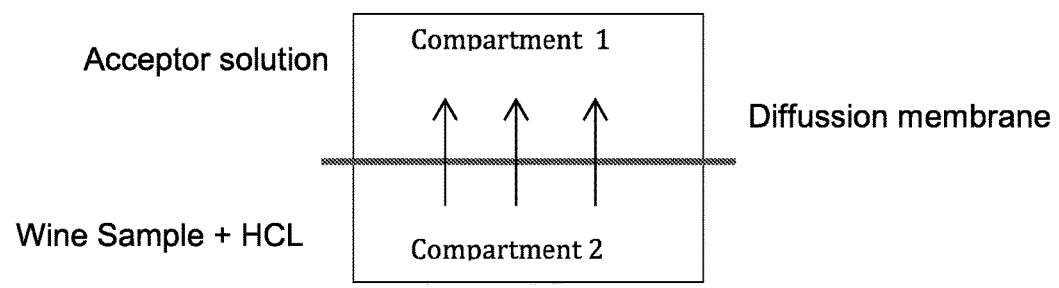
FIG. 4 represents a diagram of the diffusion process between chamber 1 (or compartment 1) and chamber 2 (or compartment 2) using wine in order to measure the level of free SO$_2$ in the wine. A bisulfite acceptor solution is in chamber 1 and wine plus an acid such as HCL is in chamber 2. The wine pH level is lowered so the bisulfite in the wine turns into its gaseous state of SO$_2$ and passes through the membrane into the bisulfite acceptor solution in chamber 1 where the pH is measured.
Figure 5:
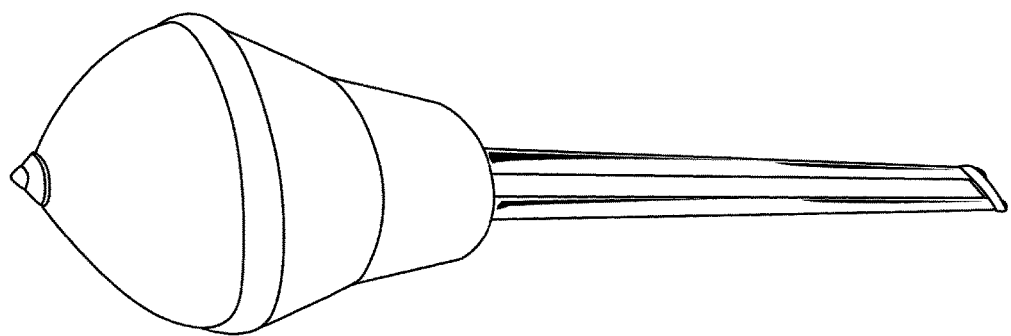
FIG. 5 represents a rendering of what the sensor might look like in a more stylized form.

The detection of SO$_2$ is based on the conversion of all the bisulfite present in wine to its gas form SO$_2$ with the acidification of the sample to pH 2 or below. Then SO$_2$ diffuses through a permeable membrane in the same way as acetic acid and it is detected indirectly by the ISFET due to pH change (see FIG. 4). This detection methodology has an important interference due to CO$_2$. This interference could be avoided by degasing the wine sample before measuring.

The wireless sensor contains two compartments separated by a diffusion membrane (e.g., GVWP04700, a Millipore Durapore membrane filter, 5). In one compartment or chamber (e.g., chamber 1), the ISFET/reference electrode will be placed. This chamber will be filled with the acceptor solution each time a measurement will be carried out. The other compartment will be filled with the sample for each measurement.

In the measurement of pH, acetic acid, and free SO$_2$ of wine as the target liquid during winemaking process, the detailed steps describing the flow of liquids through the sensor as voltage measurements are taken measuring ion concentrations, with corresponding pH values, are shown as follows (see FIG. 2):

1. There is a permeable membrane between chamber 1 and chamber 2 that allows for specific size molecules to pass between the chambers. The first process is to calibrate the ISFET chip to ensure it is taking accurate measurements. This does not need to be done each time the sensor is used, but it's recommended to be done on a frequent basis because ISFET chip accuracy tends to drift over time. To calibrate the chip, two different buffer solutions with known pH concentrations at the low end and at the high end of the target pH range are used to create a calibration curve. The ion concentration of each pH buffer solution displayed as voltage can be measured by the ISFET. By plotting the two voltage readings corresponding to the two known pH values, a calibration curve is created to determine the pH value corresponding to a voltage reading taken between the two voltages of the buffer solutions. Because wine typically has a pH in the range of 3.5, buffer solutions of pH 3 and pH 7 are used. The first buffer solution with a pH value of 3 is pumped into chamber 1 containing the ISFET. Nothing is pumped into chamber 2, it remains empty. A voltage reading is taken with the ISFET in chamber 1 establishing the voltage measurement that corresponds to a pH value of 3. The pH 3 buffer solution is then pumped out of chamber 1. Water/air/water is pumped into chamber 1 to clean out the buffer solution.
2. The second stage of the calibration is next. A pH 7 buffer solution is pumped into chamber 1. Nothing is pumped into chamber 2, it remains empty. A voltage reading is taken with the ISFET in chamber 1 establishing the voltage measurement that corresponds to a pH value of 7. The pH 7 buffer solution is then pumped out of chamber 1 and a water/air/water sequence is pumped into chamber 1 to clean it out. With a voltage measurement for pH 3 buffer solution and a voltage measurement for pH 7 buffer solution, a calibration curve is created from software on the CPU connected to the ISFET and stored in the memory of a central processing unit (CPU) so that the pH value of a liquid in chamber 1 will be determined by the voltage measurement taken by the ISFET. The calibration curve is necessary to ensure the voltage readings and corresponding pH values are accurate.
3. The next step is to measure the pH of the wine. Wine (L6) is pumped into chamber 1 and a voltage measurement is taken by the ISFET. Using the calibration curve stored in the CPU memory, a corresponding pH value is determined. The wine is then pumped out of chamber 1 and a water/air/water sequence occurs to clean out chamber 1.
4. The next step is to measure the acetic acid concentration. The acetic acid carrier solution (L1) with a known pH value is pumped into chamber 1 and wine (L6) is pumped into chamber 2. The acetic acid molecules in the wine pass through the membrane from chamber 2 to chamber 1 when the wine is allowed to remain in chamber for approximately 10 minutes. A voltage reading is taken using the ISFET in chamber 1 and a corresponding pH value is determined. The change in pH value of the acetic acid carrier solution before entering chamber 1 and the resulting pH value after acetic acid molecules diffuse across the membrane from the wine determines the acetic acid concentration of the wine. Once the voltage measurement is taken, the fluids are pumped out of each chamber and each chamber is cleaned with a water/air/water sequence.
5. The next step is to measure free $SO_2$. The $SO_2$ carrier solution (L2) with a known pH value is pumped into chamber 1 and wine (L6) along with the HCl solution (L5) are pumped into chamber 2. The combined pH value of the L6 plus L5 will be pH 2 or less. Bisulfite in the wine must be turned into a gaseous state of $SO_2$ in order for the molecules to diffuse across the membrane between the chambers in order for the $SO_2$ level of the wine to be determined. The solutions stay in chambers 1 and 2 for approximately 10 minutes allowing the $SO_2$ molecules to pass across the membrane, then the voltage of the $SO_2$ carrier solution is taken with the ISFET in chamber 1 and the corresponding pH value determined using the stored calibration curve. The change in pH value of the $SO_2$ carrier solution before entering chamber 1 and the resulting pH value after the $SO_2$ molecules pass through the membrane is used to determine the free $SO_2$ concentration in the wine. After the voltage measurement is taken, both chambers are pumped out and each chamber is cleaned with a water/air/water sequence.
6. The final step is to fill chamber 1 and chamber 2 with pH 3 buffer solution for storage per the manufacturer's recommendation for longevity of the ISFET.

The design includes a replaceable cartridge containing all of the consumable fluids (pH 3 buffer, pH 7 buffer, acetic acid carrier solution, $SO_2$ carrier solution, HCl, and Deionized (DI) water) along with an empty space for storage of the waste that is pumped out after each test. The cartridge is then disposed when the fluids are empty and the waste containment area is full. The volume of fluids and sample needed for a certain period will depend on the compartment volume and the number of measurements.

In addition to the detection of pH, acetic acid and free $SO_2$, the sensor will contain a central processing unit (CPU) with other electronics that allow for the detection of physical properties of the target liquid in the container, including temperature, liquid level, physical location and movement, with all data communicated wirelessly to a cloud based server which is accessible through the internet on mobile devices. The target liquid can be any aqueous solution and is not limited to alcoholic beverage such as wine, spirits and beer. The target analysis is not limited to pH, acetic acid, and free $SO_2$. The aforementioned processes can be used to detect other chemistry and properties of a liquid depending on the test chemistry configuration used.

As used herein, "a" or "an" means one or more (or at least one).

All illustrations of the drawings are for the purpose of describing selected version of the present invention and are not intended to limit the scope of the present invention.

Although the invention has been explained in relation to its preferred embodiment, it is to be understood that many other possible modifications and variations can be made without departing from the spirit and scope of the invention as hereinafter claimed.

REFERENCES

1. Mainwaring A., Polastre, J., Szewczyk R., Culler D., and Anderson J. Wireless sensor networks for habitat monitoring. WSNA pages 88-97, Sep. 28, 2002.
2. Jimenez-Jorquera, C., Orozco, J. and Baldi A. ISFET based microsensor for environmental monitoring, Sensors 10 61-83 (2010),
3. Alegret S., Bartroli, J., Jimenez C., del Valle, M., Dominguez, C., Cabruja, E., Merlos, A. Flow-through pH-ISFET as detector in automated determinations. Electroanalysis vol. 3 (4-5), 349-354 (1991).
4. Bartroli J., Escalada M., Jimenez-Jorquera C. and Alonso J. Determination of total and free sulfur dioxide in wine by flow injection analysis and gas-diffusion using p-aminoiazobenzene as the colorimetric reagent. Anal. Chem. 63(21) 2532-2535 (1991).
5. Web site for Durapore membrane filter: http://www.emdmillipore.com/US/en/product/Durapore-Membrane-Filter,MM_NF-GVWP04700.

What is claimed is:

1. An apparatus for detecting and measuring properties of a target liquid, the apparatus comprising:
   an enclosure configured to couple to a container holding the target liquid, the enclosure including a first chamber and a second chamber, wherein the enclosure includes:
      a permeable membrane located in the enclosure and separating the first chamber and the second chamber,
      an ion selective field effect transistor (ISFET) chip located in the first chamber, and
      a pump system,
   one or more probes coupled to the pump system and extending through at least a portion of the enclosure; and
   a bung, wherein the enclosure is mounted on a top of the bung and the one or more probes protrude from the bung a predetermined distance, wherein the pump system is configured to pump an acetic acid solution having a known pH value into the first chamber and the target liquid into the second chamber, the ISFET chip is configured to take a voltage measurement, and wherein a resulting pH value of the acetic acid solution after the acetic acid molecules of the target liquid diffused through the permeable membrane from the second chamber to the first chamber is determined according to the voltage measurement.

2. The apparatus of claim 1, wherein the permeable membrane is configured to enable acetic acid molecules of the target liquid to diffuse through the permeable membrane from the second chamber to the first chamber.

3. The apparatus of claim 1, wherein an acetic acid concentration of the target liquid is determined based on a change in the known pH value of the acetic acid solution and the resulting pH value of the acetic acid solution after the acetic acid molecules of the target liquid diffused through the permeable membrane from the second chamber to the first chamber.

4. The apparatus of claim 1, wherein the pump system is configured to pump (i) a sulfur dioxide solution having a known pH value into the first chamber, and (ii) the target liquid and an acidic solution into the second chamber, and the ISFET chip is configured to take a voltage measurement, and wherein a resulting pH value of the sulfur dioxide solution after sulfur dioxide molecules diffused through the permeable membrane from the second chamber to the first chamber is determined according to the voltage measurement.

5. The apparatus of claim 4, wherein the permeable membrane is configured to enable sulfur dioxide molecules to diffuse through the permeable membrane the second chamber to the first chamber.

6. The apparatus of claim 4, wherein a free sulfur dioxide concentration of the target liquid is determined based on a change in the known pH value of the sulfur dioxide solution and the resulting pH value of the sulfur dioxide solution after the sulfur dioxide molecules diffused through the permeable membrane from the second chamber to the first chamber.

7. The apparatus of claim 1, further comprising:
   circuitry located in the enclosure and configured to (i) determine one or more pH levels according to one or more measurements and a stored calibration curve that correlates voltage levels to pH levels, and (ii) wirelessly transmit the one or more pH levels via a network.

8. The apparatus of claim 1, wherein the target liquid is an alcoholic liquid.

9. The apparatus of claim 1, wherein the apparatus is configured to couple to an opening of the container such that the one or more probes are configured to extend from the apparatus into the target liquid.

10. A method of detecting and measuring properties of a target liquid, the method comprising:
    pumping a first solution into a first chamber of a sensing device, wherein the first solution has a known pH value and the first chamber includes an ion selective field effect transistor (ISFET) chip;
    pumping the target liquid into a second chamber of the sensing device, wherein a permeable membrane separates the first chamber and the second chamber;
    taking, by the ISFET chip, a voltage measurement; and
    determining a second pH value of the first solution according to the voltage measurement.

11. The method of claim 10, wherein the voltage measurement is taken following a predetermined time sufficient to enable a set of molecules to diffuse across the permeable membrane from the second chamber to the first chamber.

12. The method of claim 11, wherein the first solution is an acetic acid solution and the set of molecules includes acetic acid molecules.

13. The method of claim 12, further comprising:
    determining an acetic acid concentration of the target liquid based on a change in the known pH value of the first solution and the second pH value of the first solution after the set of molecules diffused through the permeable membrane from the second chamber to the first chamber.

14. The method of claim 11, wherein the first solution is a sulfur dioxide solution and the set of molecules includes sulfur dioxide molecules.

15. The method of claim 14, further comprising:
    determining free sulfur dioxide concentration of the target liquid based on a change in the known pH value of the first solution and the second pH value of the first solution after the set of molecules diffused through the permeable membrane from the second chamber to the first chamber.

16. The method of claim 11, wherein the sensing device is configured to couple to an opening of a container holding the target liquid, and the sensing device includes a pump system and one or more probes, wherein the pump system pumps the target liquid into the second chamber through the one or more probes.

17. The method of claim 10, wherein the target liquid is an alcoholic liquid.

18. The apparatus of claim 17, wherein the ISFET chip is included within a wireless sensor, the wireless sensor including circuitry configured to determine at least one of (i) liquid level of the target liquid in the container according to measurements from liquid level sensor, or (ii) a temperature of the target liquid.

19. An apparatus for detecting and measuring properties of a target liquid, the apparatus comprising:
    an enclosure configured to couple to a container holding the target liquid, the enclosure including a first chamber and a second chamber, wherein the enclosure includes:

a permeable membrane located in the enclosure and separating the first chamber and the second chamber, a pump system configured to pump a sulfur dioxide solution having a known pH value into the first chamber and the target liquid into the second chamber, wherein a free sulfur dioxide concentration of the target liquid is determined based on a difference between the known pH value of the sulfur dioxide solution and a resulting pH value of the sulfur dioxide solution after sulfur dioxide molecules diffused through the permeable membrane from the second chamber to the first chamber, and an ion selective field effect transistor (ISFET) chip located in the first chamber configured to take voltage measurements;

one or more probes coupled to the pump system and extending through at least a portion of the enclosure; and a bung, wherein the enclosure is mounted on a top of the bung and the one or more probes protrude from the bung a predetermined distance.

20. The apparatus of claim 19, wherein the target liquid is an alcoholic liquid.

\* \* \* \* \*